United States Patent [19]
Chiao et al.

[11] Patent Number: 5,980,459
[45] Date of Patent: Nov. 9, 1999

[54] ULTRASOUND IMAGING USING CODED EXCITATION ON TRANSMIT AND SELECTIVE FILTERING OF FUNDAMENTAL AND (SUB)HARMONIC SIGNALS ON RECEIVE

[75] Inventors: Richard Yung Chiao, Clifton Park, N.Y.; Ann Lindsay Hall, New Berlin, Wis.; Kai Erik Thomenius, Clifton Park, N.Y.

[73] Assignee: General Electric Company, Schenectady, N.Y.

[21] Appl. No.: 09/052,675

[22] Filed: Mar. 31, 1998

[51] Int. Cl.$^6$ ................................................ A61B 8/00
[52] U.S. Cl. .......................................... 600/447; 600/458
[58] Field of Search .................................... 600/437, 440, 600/443–447, 458

[56] References Cited

U.S. PATENT DOCUMENTS

| | | | |
|---|---|---|---|
| 5,010,885 | 4/1991 | Fink et al. | 73/625 |
| 5,456,257 | 10/1995 | Johnson et al. | 600/458 |
| 5,632,277 | 5/1997 | Chapman et al. | 128/660.07 |
| 5,706,819 | 1/1998 | Hwang et al. | 600/458 |
| 5,833,613 | 11/1998 | Averkiou et al. | 600/440 |
| 5,833,614 | 11/1998 | Dodd et al. | 600/447 |

OTHER PUBLICATIONS

Averkiou et al., "Ultrasonic Diagnostic Imaging of Response Frequency Differing from Transmit Frequency" EP 0851241 published Jan. 07, 1998 Bulletin 1998/27.

Powers, J.E. et al. "Ultrasonic Diagnostic Imaging with Contrast Agents", EP 0770 352 published May 2, 1997 Bulletin 1997/18.

O'Donnell, Matthews "Coded Excitation System for Improving the Penetration of Real–Time Phased–Array Imaging Systems" IEEE UFFC Trans V. 39 No. 3 May 1992.

Takecuhi, Y. "Coded Excitation for Harmonic Imaging " 1996 IEEE UTS Symp. pp. 1433–1435.

de Jong et al., "Principles and Recent Developments in Ultrasound Contrast Agents," Ultrasonics, vol. 29, pp. 324–330. (1991).

Averkiou et al., "A New Imaging Technique Based on the Nonlinear Properties of Tissue," Proc. 1997 IEEE Ultrason. Symp.

*Primary Examiner*—Francis J. Jaworski
*Attorney, Agent, or Firm*—Marvin Snyder; Douglas E. Stoner

[57] ABSTRACT

A method and an apparatus for selectively performing contrast harmonic imaging, tissue harmonic imaging and B-mode flow imaging with an ultrasound imaging system utilizes phase-coded excitation on transmit and selective firing-to-firing, i.e., "slow-time", filtering on receive. "Slow-time" filtering in combination with transmit phases which change over the set of transmit firings results in different effective "slow-time" filters corresponding to the different harmonic modes within the reflected signal. The transmit phases and the "slow-time" filter weightings are designed to selectively enhance the desired modes while substantially suppressing other modes.

23 Claims, 7 Drawing Sheets

ULTRASOUND IMAGING USING CODED EXCITATION ON TRANSMIT AND SELECTIVE FILTERING OF FUNDAMENTAL AND (SUB)HARMONIC SIGNALS ON RECEIVE

FIELD OF THE INVENTION

This invention generally relates to ultrasound imaging of the human anatomy for the purpose of medical diagnosis. In particular, the invention relates to methods and apparatus for imaging tissue harmonics and methods and apparatus for imaging fluid flow with or without contrast agents.

BACKGROUND OF THE INVENTION

Conventional ultrasound scanners create two-dimensional B-mode images of tissue in which the brightness of a pixel is based on the intensity of the echo return. Conventional B-mode images are formed from a combination of fundamental and harmonic signal components, the former being direct echoes of the transmitted pulse and the latter being generated in a nonlinear medium such as tissue from finite-amplitude ultrasound propagation. In certain instances, e.g., obese patients, ultrasound images can be improved by suppressing the fundamental and emphasizing the harmonic signal components.

Tissue harmonic imaging was proposed in an article by Averkiou et al. entitled, "A new imaging technique based on the nonlinear properties of tissues," Proc. 1997 IEEE Ultrasonic Symp. Propagation of sound beams in biological tissues is known to be nonlinear, giving rise to the generation of harmonics. In tissue harmonic imaging, energy is transmitted at a fundamental frequency $f_0$ and an image is formed with energy at the second harmonic $2f_0$. Some of the characteristics of the nonlinearly generated second harmonic beams are a narrower beam, lower sidelobes than the fundamental and beam formation in a cumulative process, i.e., the second harmonic continually draws energy from the fundamental during propagation. These characteristics contribute to axial resolution improvements, reduction of multiple reflections due to tough windows, and clutter reduction due to inhomogeneities in the tissue and skin layers.

Conventional ultrasound imaging systems also have a so-called "color flow" mode in which the flow of blood or movement of tissue can be imaged. Conventional ultrasound flow imaging methods use either the Doppler principle or a time-domain cross-correlation method to estimate the average flow velocity, which is then displayed in color overlaid on a B-mode image.

Measurement of blood flow in the heart and vessels using the Doppler effect is well known. The frequency shift of backscattered ultrasound waves may be used to measure the velocity of the backscatterers from tissue or blood. The change or shift in backscattered frequency increases when blood flows toward the transducer and decreases when blood flows away from the transducer. The Doppler shift may be processed to estimate the average flow velocity, which is displayed using different colors to represent speed and direction of flow. The color flow velocity mode displays hundreds of adjacent sample volumes simultaneously, all color-coded to represent each sample volume's velocity.

In accordance with a known imaging system, the color flow mode employs multiple transmit firings for each focal point. Operating on a packet of as many as 16 transmits, a high-pass wall filter rejects echoes from slow-moving tissue or vessel walls to reduce the signal dynamic range for subsequent flow processing, using the Kasai autocorrelation algorithm or a cross-correlation algorithm to estimate the average flow velocity.

Although quantitative velocity information may be obtained in conventional color-flow imaging, the ability to see physical flow is limited by its clutter rejection capability, resolution, frame rate, and axial-only flow sensitivity.

Digital subtraction methods have been previously proposed to image moving reflectors in B-mode imaging (see Ishihara et al., "Path Lines in Blood Flow Using High-Speed Digital Subtraction Echography," Proc. 1992 IEEE Ultrason. Symp., pp. 1277–1280, and Ishihara et al., "High-Speed Digital Subtraction Echography: Principle and Preliminary Application to Arteriosclerosis, Arrhythmia and Blood Flow Visualization," Proc. 1990 IEEE Ultrason. Symp., pp. 1473–1476). However, these methods use frame-to-frame subtraction, which results in a wall filter having an extremely low cutoff frequency. The low cutoff frequency is due to the long time delay between adjacent frames, which does not adequately suppress signals from slow-moving tissue or vessel walls.

U.S. Pat. No. 5,632,277 to Chapman et al. discloses a nonlinear imaging system using phase inversion subtraction. The Chapman patent uses "first and second ultrasound pulses that are alternatively transmitted into the specimen being imaged," and mentions the particular embodiment of transmitting and summing on receive two pulses that differ by 180°.

Contrast agents have been developed for medical ultrasound to aid in diagnosis of traditionally difficult-to-image vascular anatomy. For example, the use of contrast agents is discussed by de Jong et al. in "Principles and Recent Developments in Ultrasound Contrast Agents," Ultrasonics, Vol. 29, pp. 324–380 (1991). The agents, which are typically microbubbles whose diameter is in the range of 1–10 micrometers, are injected into the blood stream. Since the backscatter signal of the microbubbles is much larger than that of blood cells, the microbubbles are used as markers to allow imaging of blood flow. One method to further isolate echoes from these agents is to use the (sub)harmonic components of the contrast echo, which is much larger than the harmonic components of the surrounding tissue without contrast agent. [See, e.g., Newhouse et al., "Second Harmonic Doppler Ultrasound Blood Perfusion Measurement," Proc. 1992 IEEE Ultrason. Symp., pp. 1175–1177; and Burns, et al., "Harmonic Power Mode Doppler Using Microbubble Contrast Agents: An Improved Method for Small Vessel Flow Imaging," Proc. 1994 IEEE Ultrason. Symp., pp. 1547–1550.]

U.S. Pat. No. 5,706,819 to Hwang et al. discloses a method and an apparatus for ultrasonic imaging using harmonic contrast agents, e.g., gas-filled microbubbles. Ultrasonic pulses of opposite polarity are transmitted in successive firings. The respective echo signals are summed to extract the harmonic response attributable to the injected contrast agents.

There is a need for a method of contrast harmonic imaging in which fundamental or second harmonic signals from contrast flow can be visualized with suppressed background tissue signals and little motion flash artifacts. This requires the imaging system to have high dynamic range, the ability to reject clutter from stationary or slow moving tissue and vessel walls, high resolution, high frame rate, and flow sensitivity in all directions. A need also exists for a method of tissue harmonic imaging in which harmonic signals generated by nonlinear propagation in tissue are visualized. In addition, a need exists for a method of visualizing fundamental signals from blood flow (without contrast agents) in B mode with minimal motion flash artifacts. A further need exists for a programmable ultrasound imaging system capable of selectively performing contrast harmonic imaging, tissue harmonic imaging and B-mode flow imaging.

SUMMARY OF THE INVENTION

A method and apparatus are provided for selectively performing contrast harmonic imaging, tissue harmonic imaging and B-mode flow imaging wherein the preferred embodiments use phase-coded excitation on transmit and selective firing-to-firing, i.e., "slow-time", filtering on receive. "Slow-time" filtering in combination with transmit phases which change over the set of transmit firings results in different harmonic effective "slow-time" filters corresponding to the different harmonic modes within the reflected signal. The transmit phases and the "slow-time" filter weightings are designed to selectively enhance the desired modes while suppressing others. In particular, a sequence of broadband pulses with different phases (and possibly different amplitudes) are transmitted to a transmit focal position over multiple firings, and the set of received beamformed signals are multiplied with a set of (possibly complex) scalar weightings before summing together that set of weighted beamformed signals for subsequent processing to form one image scan line. A complete image is formed by repeating this procedure for multiple transmit focal positions across the region of interest.

In accordance with a preferred embodiment of the invention, the "slow-time" filter is embodied as a finite impulse response (FIR) filter which receives a first set of filter coefficients for filtering the receive signal produced as a result of a first phase-encoded transmit firing, and which receives a second set of filter coefficients for filtering the receive signal produced as a result of a second phase-encoded transmit firing. The first set of filter coefficients is formed by multiplying each of a predetermined set of filter coefficients by a first scalar weighting; the second set of filter coefficients is formed by multiplying each of the predetermined set of filter coefficients by a second scalar weighting. The transmit phases and the "slow-time" scalar weightings are programmable as a function of the three different applications, namely, contrast harmonic imaging, tissue harmonic imaging and B-mode flow imaging.

In contrast harmonic imaging, the sonographer wishes to see fundamental or second harmonic signals from contrast flow with suppressed background tissue signals and little motion flash artifacts. This can be achieved in the following ways: (1) by high-pass filtering the second harmonic and suppressing a substantial fraction of the fundamental signal, which results in good suppression of background tissue signals; (2) by high-pass filtering the fundamental and second harmonic signals, which results in good background suppression and better low flow sensitivity but larger motion flash artifacts; or (3) by high-pass filtering or suppressing the fundamental and all-pass filtering the second harmonic, which results in more tissue background (from the second harmonic) but shows harmonic signals from even the slowest-moving contrast agents.

In tissue harmonic imaging, the goal is to see harmonic signals (in particular, the second harmonic) generated by nonlinear propagation in tissue. This is achieved by suppressing a substantial fraction of the fundamental signal and passing a substantial fraction of the second harmonic signal.

Finally, the goal in B-mode flow imaging is to visualize fundamental signals from blood flow (without contrast agents) with minimal motion flash artifacts. This is accomplished by high-pass filtering the fundamental and all-pass filtering the second harmonic, which smoothes out flash artifacts.

The "slow-time" filtering is preferably performed by an FIR filter with B-mode image feed-through. The "slow-time" or firing-to-firing filtering permits a longer FIR filter for better clutter suppression, while increasing the cutoff frequency to a useful range compared with frame-to-frame firing and filtering.

BRIEF DESCRIPTION OF THE DRAWINGS

FIG. 4) [0°, 180°, 0°, 180°] and [0.4, 1, 1, 0.4]; FIG. 5) [0°, 90°, 0°, 180°] and [0.4, 1, 1, 0.4] (with "slow-time" filter phases [0°, 90°, 0°, 0°]); FIG. 6) [0°, 180°, 180°, 0°] and [0.4, 1, −1, −0.4]; FIG. 7) [0°, 180°] and [1, 1]; FIG. 8) [180°, 0°, 180°] and [0.5, 1, 0.5]; FIG. 9) [0°, 0°, 180°, 180°] and [1, 1, 1, 1]; FIG. 10) [0°, 180°, 180°, 0°] and [1, 1, 1, 1]; and FIG. 11) [0°, 180°, 0°, 180°] and [1, 1, −1, −1].

DETAILED DESCRIPTION OF THE PREFERRED EMBODIMENTS

Figure 1:
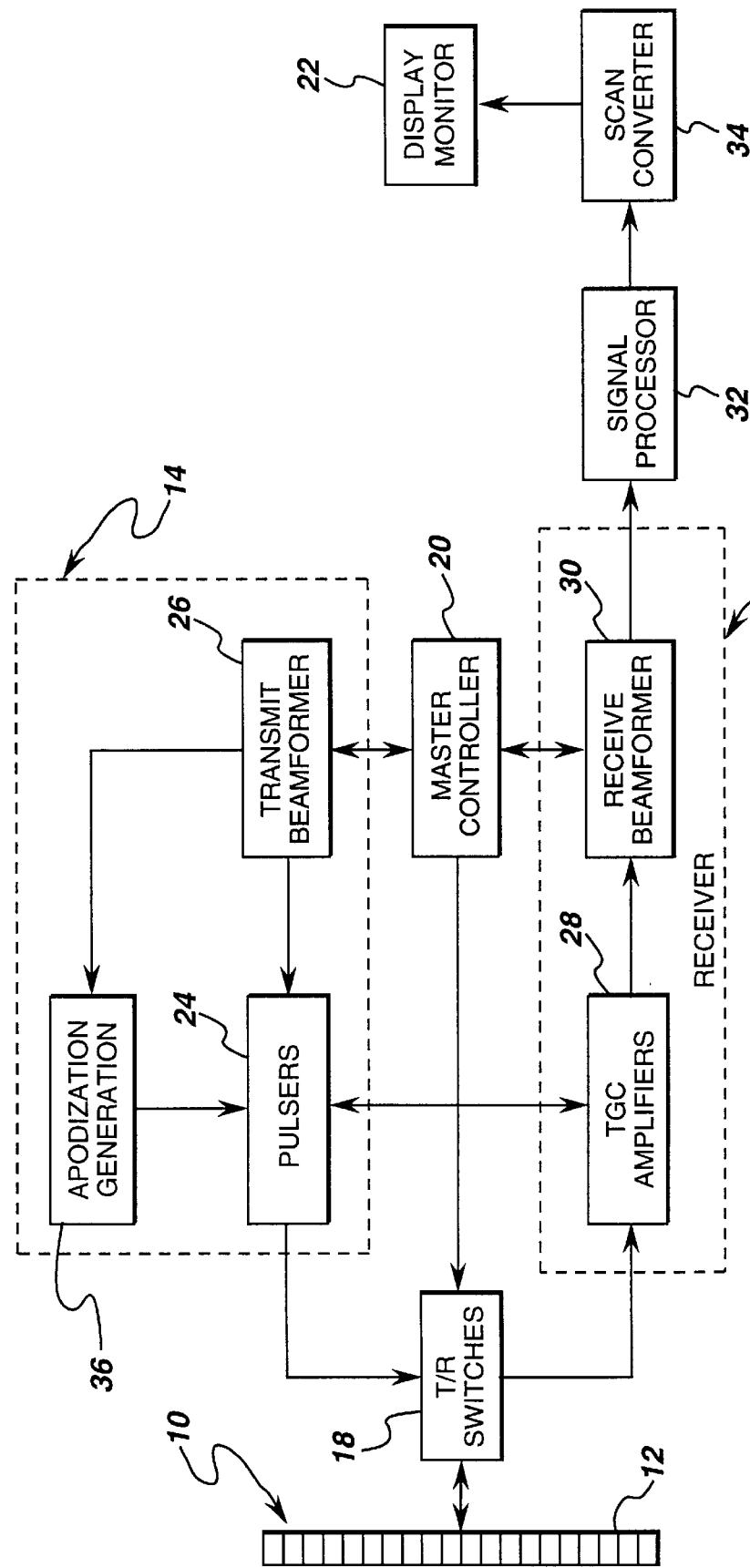
FIG. 1 is a block diagram of a conventional ultrasound imaging system.

The present invention can be incorporated in an ultrasonic imaging system of the type depicted in FIG. 1. This imaging system comprises a transducer array 10 comprising a plurality of separately driven transducer elements 12, each of which produces a burst of ultrasonic energy when energized by a pulsed waveform produced by a transmitter 14. The ultrasonic energy reflected back to transducer array 10 from the object under study is converted to an electrical signal by each receiving transducer element 12 and applied separately to a receiver 16 through a set of transmit/receive (T/R) switches 18. T/R switches 18 are typically diodes which protect the receive electronics from the high voltages generated by the transmit electronics. The transmit signal causes the diodes to shut off or limit the signal to the receiver. Transmitter 14 and receiver 16 are operated under control of a master controller 20 responsive to commands by a human operator. A complete scan is performed by acquiring a series of echoes in which transmitter 14 is gated ON momentarily to energize each transducer element 12, and the subsequent echo signals produced by each transducer element 12 are applied to receiver 16. A channel may begin reception while another channel is still transmitting. Receiver 16 combines the separate echo signals from each transducer element to produce a single echo signal which is used to produce a line in an image on a display monitor 22.

Under the direction of master controller 20, transmitter 14 drives transducer array 10 such that the ultrasonic energy is transmitted as a directed focused beam. To accomplish this, respective time delays are imparted to a plurality of pulsers 24 by a transmit beamformer 26. Master controller 20 determines the conditions under which the acoustic pulses will be transmitted. With this information, transmit beamformer 26 determines the timing and amplitudes of each of the transmit pulses to be generated by pulsers 24. The amplitudes of each transmit pulse are generated by an apodization generation circuit 36, which may be a high-voltage controller that sets the power supply voltage to each pulser. Pulsers 24 in turn send the transmit pulses to each of elements 12 of transducer array 10 via T/R switches 18, which protect time-gain control (TGC) amplifiers 28 from the high voltages which may exist at the transducer array. By appropriately adjusting the transmit focus time delays in a conventional manner and also adjusting the apodization weightings, an ultrasonic beam can be directed and focused to form a transmit beam.

The echo signals produced by each burst of ultrasonic energy reflect from objects located at successive ranges along each transmit beam. The echo signals are sensed separately by each transducer element 12 and a sample of the magnitude of the echo signal at a particular point in time represents the amount of reflection occurring at a specific range. Due to differences in the propagation paths between a reflecting point and each transducer element 12, the echo signals will not be detected simultaneously and their amplitudes will not be equal. Receiver 16 amplifies the separate echo signals via a respective TGC amplifier 28 in each receive channel. The amplified echo signals are then fed to a receive beamformer 30. Each receiver channel of the receive beamformer is coupled to a respective one of transducer elements 12 by a respective TGC amplifier 28.

Under the direction of master controller 20, receive beamformer 30 tracks the direction of the transmitted beam, sampling the echo signals at a succession of ranges along each beam. Receive beamformer 30 imparts the proper time delay to each amplified echo signal, provides dynamic apodization on receive and sums the delayed and apodized echo signals to provide a summed echo signal which accurately indicates the total ultrasonic energy reflected from a point located at a particular range along one ultrasonic beam. The receive focus time delays are computed in real-time using specialized hardware or are read from a look-up table. The receive channels also have circuitry for filtering the received pulses. The time-delayed receive signals are then summed and supplied to a signal processor 32. Signal processor 32 converts the summed receive signals to display data. In the B-mode (grey-scale), this is the envelope of the signal with some additional processing, such as edge enhancement and logarithmic compression. A scan converter 34 receives the display data from signal processor 32 and converts the data into the desired image for display. In particular, scan converter 34 converts the acoustic image data from polar coordinate (R-θ) sector format or Cartesian coordinate linear array to appropriately scaled Cartesian coordinate display pixel data at the video rate. These scan-converted acoustic data are then provided for display on display monitor 22, which images the time-varying amplitude of the signal envelope as a grey scale.

Figure 2:
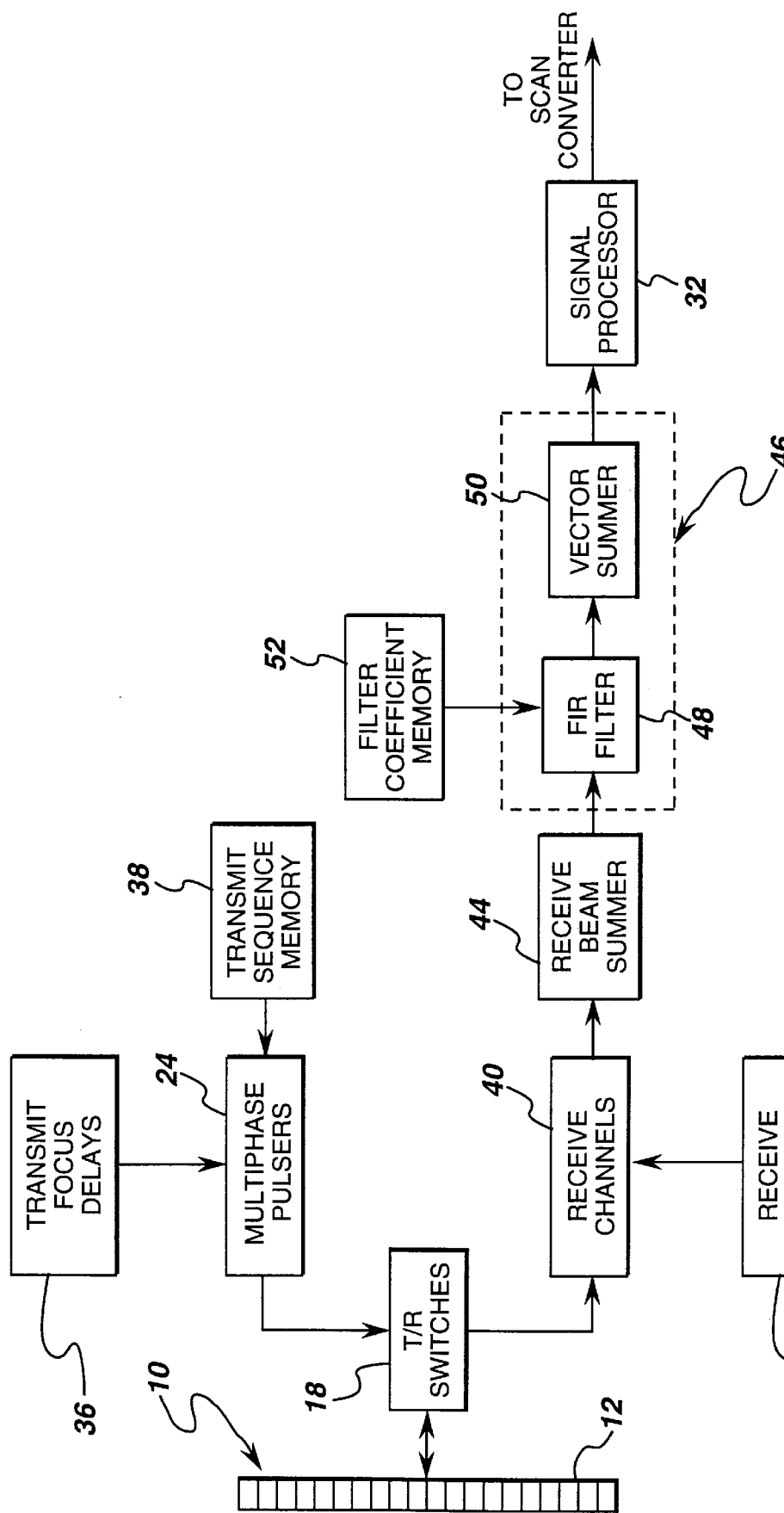
FIG. 2 is a block diagram of portions of an ultrasound imaging system in accordance with a preferred embodiment of the invention.

FIG. 2 shows portions of an ultrasound imaging system in accordance with the present invention. In this system each transducer element in the transmit aperture is pulsed N times by a respective multiphase (e.g., bipolar) pulser 24' in accordance with transmit codes stored in a transmit sequence memory 38. For example, the transducer elements are pulsed in accordance with a first transmit code during a first transmit firing and in accordance with a second transmit code during a second transmit firing, wherein the first and second transmit codes are applied as phase coding (e.g., polarity reversal) to a conventional transmit pulse. Pulsers 24' drive elements 12 of transducer array 10 such that the ultrasonic energy produced is focused at the same transmit focal position for each transmit firing. To accomplish this, identical transmit focus time delays 36 are imparted to the respective pulsed waveforms produced by the pulsers in accordance with the transmit codes. By appropriately adjusting the transmit focus time delays in a conventional manner, the ultrasonic beams can be focused at a multiplicity of transmit focal positions to effect a scan in an image plane.

For each transmit, the echo signals from transducer elements 12 are fed to respective receive channels 40 of the receive beamformer. Under the direction of master controller 20 (FIG. 1), the receive beamformer tracks the direction of the transmitted beam. The receive beamformer imparts the proper receive focus time delays 42 to the received echo signal and sums them to provide an echo signal which accurately indicates the total ultrasonic energy reflected from a particular transmit focal position along a transmit beam. The time-delayed receive signals are summed in a receive summer 44 for each of the N transmit firings focused at a particular transmit focal position. The summed receive signal for each of the N transmit firings is then provided in succession to a "slow-time" filter 46, which filters across the N transmit firings and then supplies a filtered signal to signal processor 32. Signal processor 32 forms the envelope of this filtered signal. After post-processing (including edge enhancement and logarithmic compression) and scan conversion, a scan line is displayed on display monitor 22 (FIG. 1). This procedure is repeated so that a respective scan line is displayed for each transmit focal position (in the case of one transmit focal position for each beam angle) or for each transmit vector (in the case of multiple transmit focal positions for each transmit vector).

In accordance with the preferred embodiments of the invention, "slow-time" filter 46 comprises an FIR filter 48 having an input coupled to the output of receive summer 44, and a vector summer 50 having an input coupled to FIR filter 48 and an output coupled to signal processor 32. The FIR filter has M filter taps for receipt of a respective set of M filter coefficients for each transmit firing. The filter coefficients for the n-th transmit firing are $a_n$, $a_n c_1$, ..., $A_n C_{M-1}$, where $a_n$ is the scalar weighting for the n-th transmit firing, n=0, 1, ..., N−1, and $c_0$, $c_1$, ..., $C_{M-1}$ is a set of filter coefficients which are selected so that FIR filter 48 passes a desired frequency band in the receive signal. The scalar weightings $a_0$, $a_1$, ..., $a_{N-1}$ cause the "slow-time" filter to selectively pass or attenuate the bandpassed signals as a function of the harmonic mode and the scatterer velocities. The filter coefficients $a_n c_0$, $a_n c_1$, ..., $a_n c_{M-1}$, are supplied to the filter for each transmit firing by the master controller from a filter coefficient memory 52. For example, for the first transmit firing, the set of filter coefficients $a_0 c_0$, $a_0 c_1$, ..., $a_0 c_{M-1}$ is supplied to the FIR filter; for the second transmit firing, the set of filter coefficients $a_1 c_0$, $a_1 c_1$, ..., $a_1 c_{M-1}$ is supplied to the FIR filter; and so forth. The filter coefficients are programmable depending upon the diagnostic application. Different sets of filter coefficients can be stored in look-up tables inside the master controller memory and the desired set of coefficients can be selectable by the system operator. For applications where the number of transmit firings N=2, one or more sets of filter coefficients are stored in memory, one set of filter coefficients being transferred to the FIR filter before the first transmit firing and another set of filter coefficients being transferred to the FIR filter after the first transmit firing and before the second transmit firing (when the same scalar weighting applies to two transmit firings, the same filter coefficient set can be used for both firings). Similarly, for applications where the number of transmit firings N>2, two or more sets of filter coefficients are stored in memory. The successive FIR filter output signals for the N transmit firings are accumulated in a vector summer 50. The output signal of the vector summer then undergoes conventional B-mode processing, followed by scan conversion and display.

In accordance with a preferred embodiment of the invention, firing-to-firing (i.e., "slow-time") filtering is combined with transmit phase coding to produce an enhanced ultrasound image. The "slow-time" filter responds differently to the different modes (fundamental, second subharmonic, second harmonic, third harmonic, etc.) of the reflected signal because the transmit phases change over the set of transmit firings. This permits one to design the transmit phases and "slow-time" filter to selectively enhance the desired modes while suppressing others. In particular, if the transmitted signal has a phase term $\exp[j\theta_i]$, where $i=0$, $1, \ldots, N-1$, then the k-th (sub)harmonic has a phase term $\exp[jk^{(-1)}\theta c_i]$, $i=0, 1, \ldots, N-1$. Thus, if the "slow-time" filter coefficients are $a_i$, $i=0, 1, \ldots, N-1$, then the effective "slow-time" filter for the k-th (sub)harmonic is $a_i \exp[jk^{(-1)} \theta_i]$, $i=0, 1, \ldots, N-1$, which has a transfer function that depends on the particular mode k.

The system of the present invention has three different application areas: contrast harmonic imaging, tissue harmonic imaging and B-flow imaging. For each application, the transmit phases and "slow-time" filter weightings may be selected to achieve the desired filtering on the fundamental and the (sub)harmonics. The "slow-time" filter responses for various preferred embodiments are shown in FIGS. 4–11. The "slow-time" filter response to the fundamental mode is indicated by solid lines, to the second harmonic is indicated by dashed lines, and to the second subharmonic is indicated by dotted lines. The horizontal axis corresponds to "slow-time" normalized frequency, while the vertical axis is the magnitude of the "slow-time" filter output. The expected range of normalized operating frequencies lies in the range of ±0.2.

In contrast harmonic imaging, contrast agents made up of gas-filled microbubbles are injected into the blood to serve as markers for imaging blood flow. It is desired to see fundamental or second harmonic signals from contrast flow with suppressed background tissue signals and little motion flash artifacts. The broad-band pulses transmitted to a particular transmit focal position in sequence are phase coded. In particular, N pulses centered at frequency $f_0$ are transmitted to each transmit focal position. On receive, a "slow-time" filter extracts the (sub)harmonic flow signal over the N transmits. In particular, a set of "slow-time" filter weightings $a_0, a_1, \ldots, a_{M-1}$ are selected so that the M-tap "slow-time" FIR filter 48 passes substantially all of the desired harmonic or subharmonic frequencies in signals reflected from agents moving at certain velocities, while substantially suppressing signals at the fundamental frequencies. If the transmitted center frequency is at $f_0$, then tissue/contrast nonlinearities will generate harmonics at $kf_0$, where k is an integer greater than or equal to 2. Also, subharmonics at frequencies $f_0/k$ may be generated by contrast bubble destruction.

Figure 6:
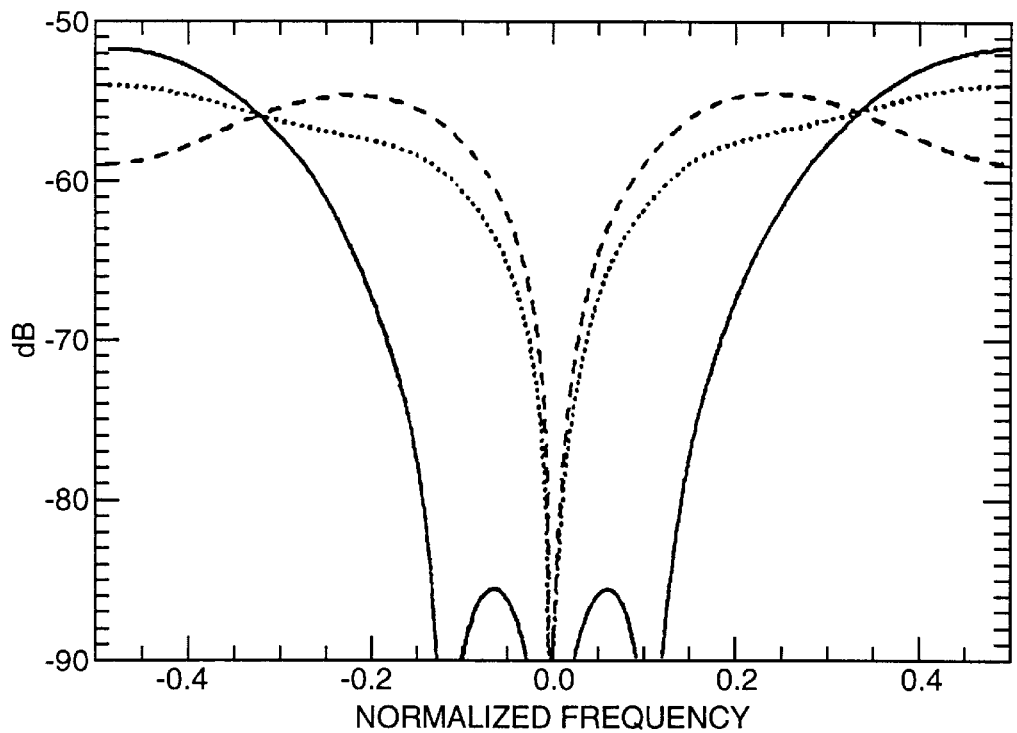
Figure 7:
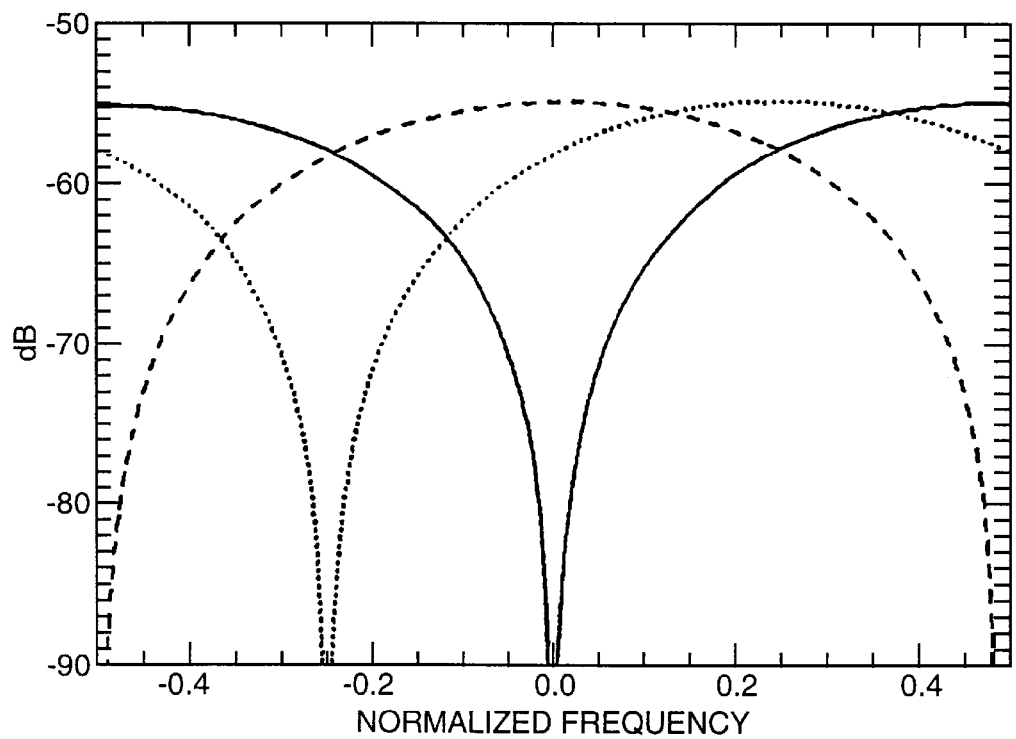
Figure 8:
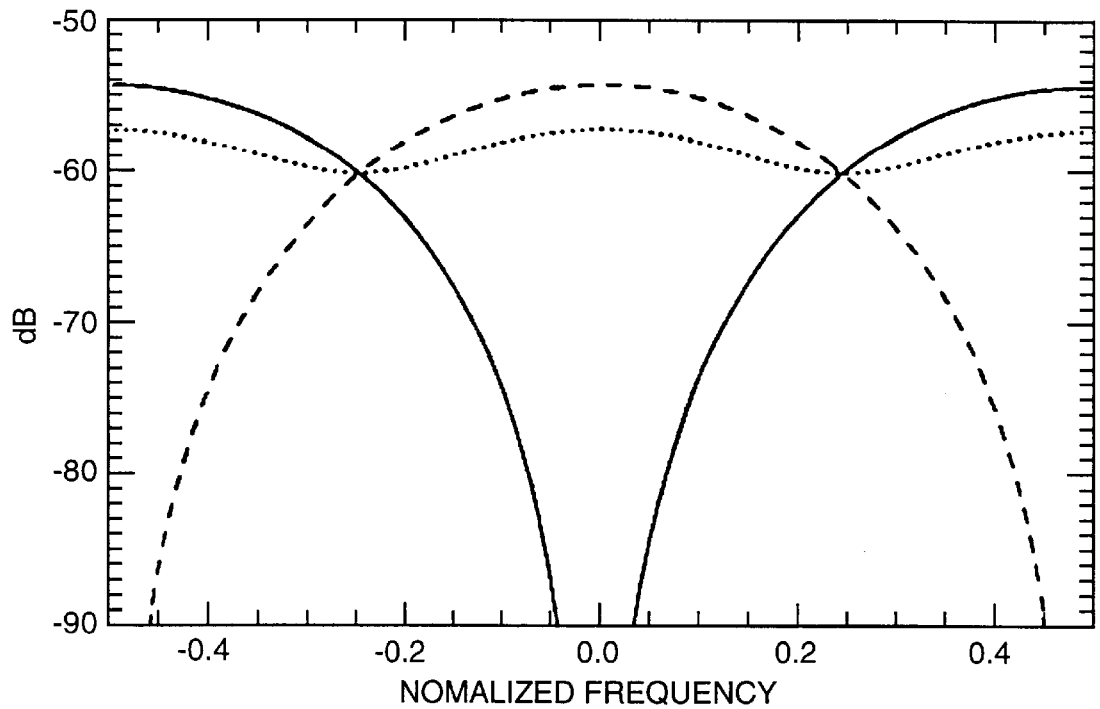
Figure 9:
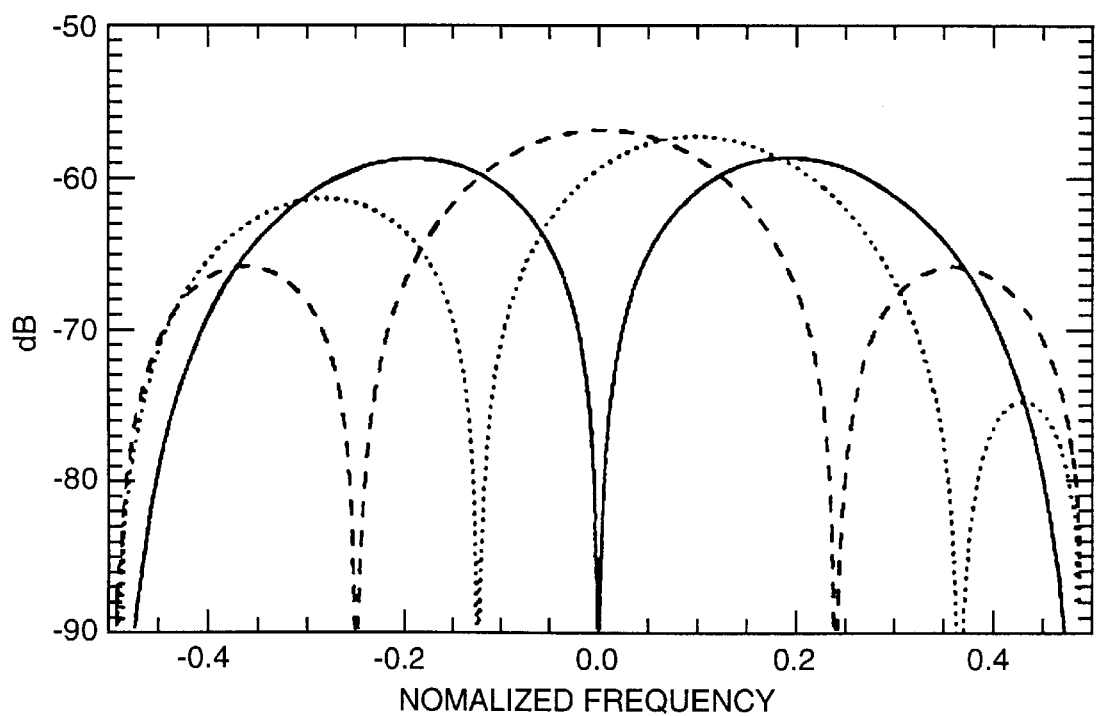
Figure 10:
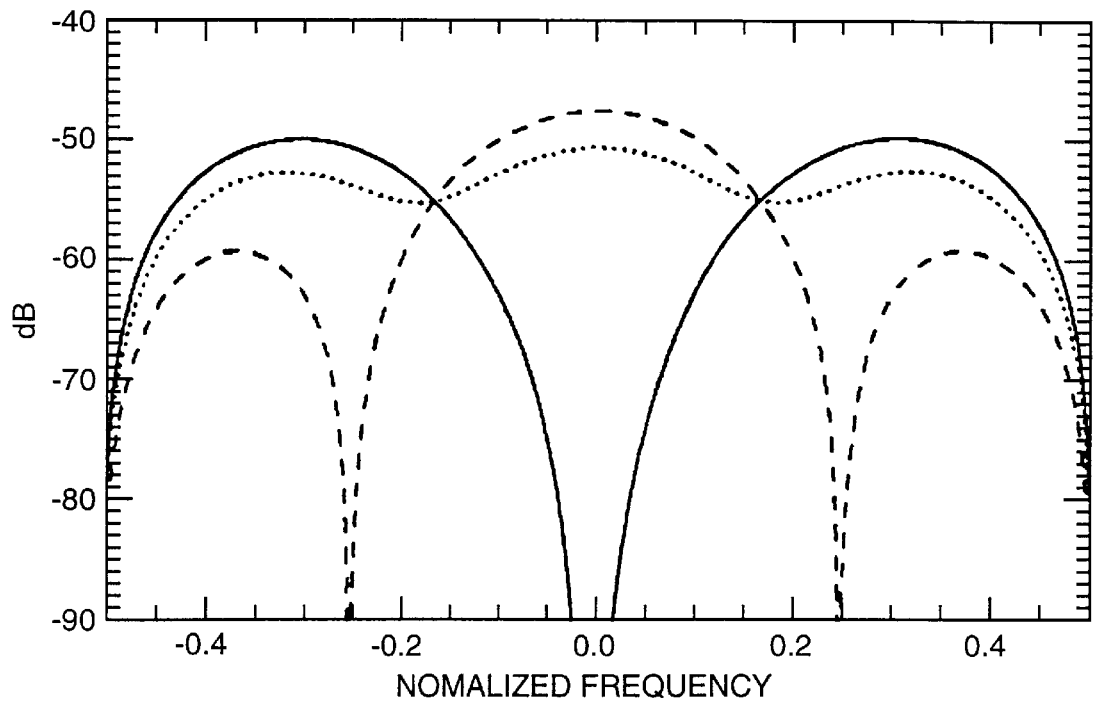

In accordance with one preferred embodiment of the invention, contrast harmonic imaging is achieved by high-pass filtering the second harmonic and suppressing all of the fundamental signal, which results in good suppression of background tissue signals, as seen in FIG. 6. The response shown in FIG. 6 was obtained using transmit phases [0°, 180°, 180°, 0°] and filter weightings [0.4, 1, −1, −0.4]. FIG. 6 shows the case wherein, in addition to suppression of the fundamental, stationary components of the (sub)harmonic signal are substantially blocked by a notch filter. This preferred embodiment is useful for nonlinear imaging of nonstationary or flow regions, and in particular for imaging contrast agents injected into the blood stream.

Figure 11:
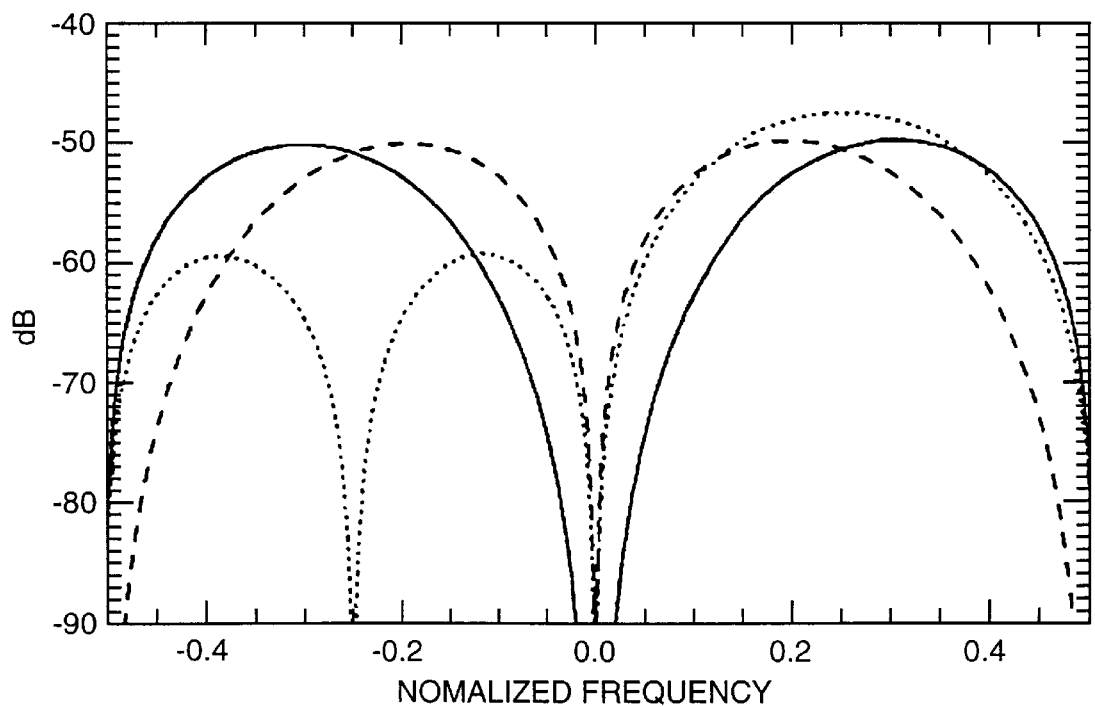

In another preferred embodiment of the invention, contrast harmonic imaging is realized by high-pass filtering of both the fundamental and the second harmonic signals, which results in better low-flow sensitivity but larger motion flash artifacts, as seen in FIG. 11. The response shown in FIG. 11 was obtained using transmit phases [0°, 180°, 0°, 180°] and filter weightings [1, 1, −1, 1].

In other preferred embodiments of the invention, contrast harmonic imaging is realized by high-pass filtering or suppressing the fundamental signal and all-pass filtering the second harmonic signal, which results in more tissue background (from the second harmonic) but shows harmonic signals from even the slowest-moving contrast agents. Examples of this mode are shown in FIGS. 4, 5 and 7–10. The response shown in FIG. 4 was obtained using transmit phases [0°, 180°, 0°, 180°] and filter weightings [0.4, 1, 1, 0.4]; the response shown in FIG. 5 was obtained using transmit phases [0°, 90°, 0°, 180°], filter weightings [0.4, 1, 1, 0.4] and filter phases [0°, 90°, 0°, 0°]; the response shown in FIG. 7 was obtained using transmit phases [0°, 180°] and filter weightings [1, 1]; the response shown in FIG. 8 was obtained using transmit phases [180°, 0°, 180°] and filter weightings [0.5, 1, 0.5]; the response shown in FIG. 9 was obtained using transmit phases [0°, 0°, 180°, 180°] and filter weightings [1, 1, 1, 1]; and the response shown in FIG. 10 was obtained using transmit phases [0°, 180°, 180°, 0°] and filter weightings [1, 1, 1, 1]. The response shown in FIG. 5 was obtained using a complex filter.

In tissue harmonic imaging, the goal is to see harmonic signals (in particular, the second harmonic) generated by nonlinear propagation in tissue. In yet another preferred embodiment of the invention, this is achieved by suppressing all of the fundamental signal and passing all of the second harmonic. To this end, the transmit phase codes and "slow-time" filter weightings represented by FIGS. 4, 5, 8 or 10 can be used. The transmit phase codes and "slow-time" filter weightings which produce the response shown in FIG. 7 can also be used, but with larger flash motion artifacts.

Finally, the goal in B-mode flow imaging is to visualize fundamental signals from blood flow (without contrast agents) with minimal motion flash artifacts. In a preferred embodiment of the invention, this is accomplished by high-pass filtering the fundamental and all-pass filtering the second harmonic. Passing the second harmonic smoothes out the flash artifacts. To this end, the transmit phase codes and "slow-time" filter weightings represented by FIGS. 7 or 9 can be used.

Figure 3:
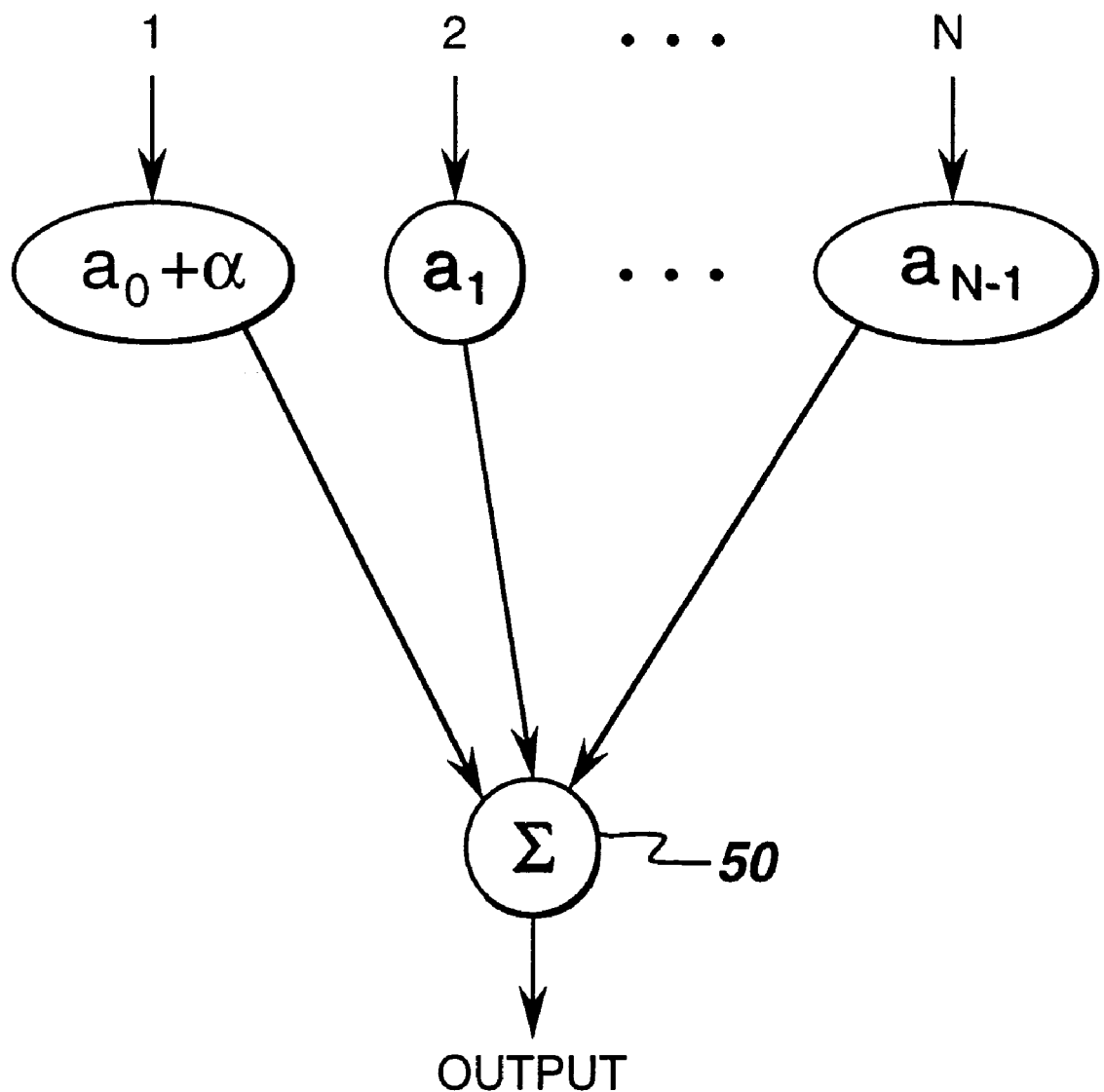
FIG. 3 is a flowchart showing "slow-time" filtering with B-mode feed-through in accordance with another preferred embodiment of the invention.
Figure 4:
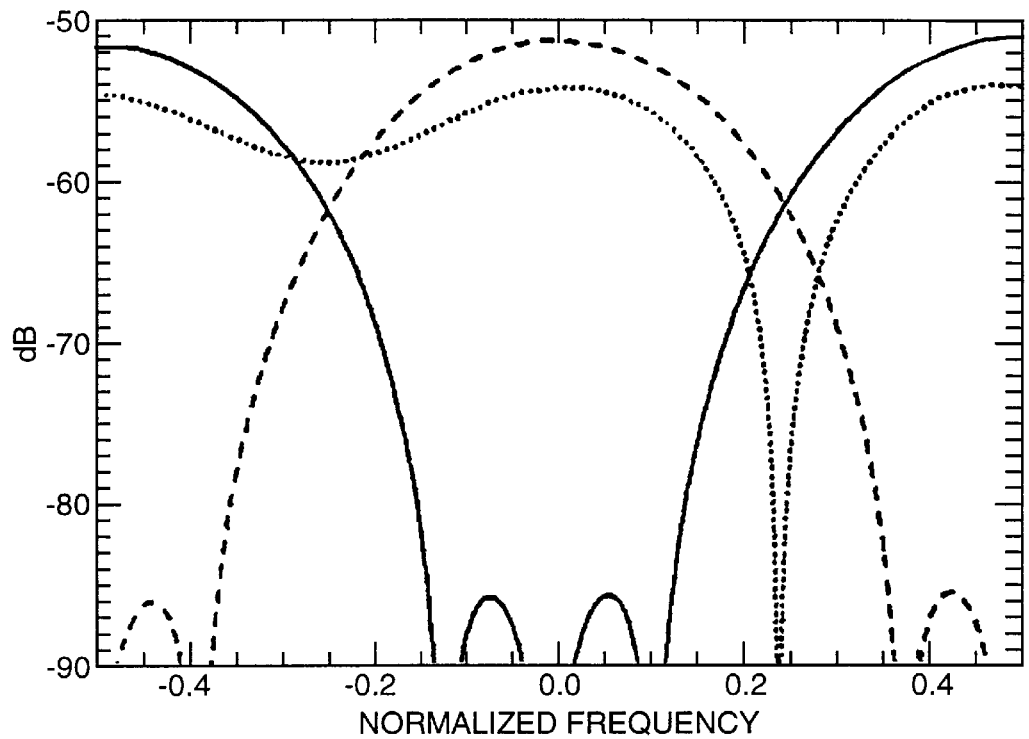
FIGS. 4, 5, 6, 7, 8, 9, 10 and 11 are graphs showing the filter response (as a function of slow-time normalized frequency) to the fundamental mode (solid lines), the second harmonic (dashed lines) and the second subharmonic (dotted lines). The transmit phases and the "slow-time" filter weightings are as follows.
Figure 5:
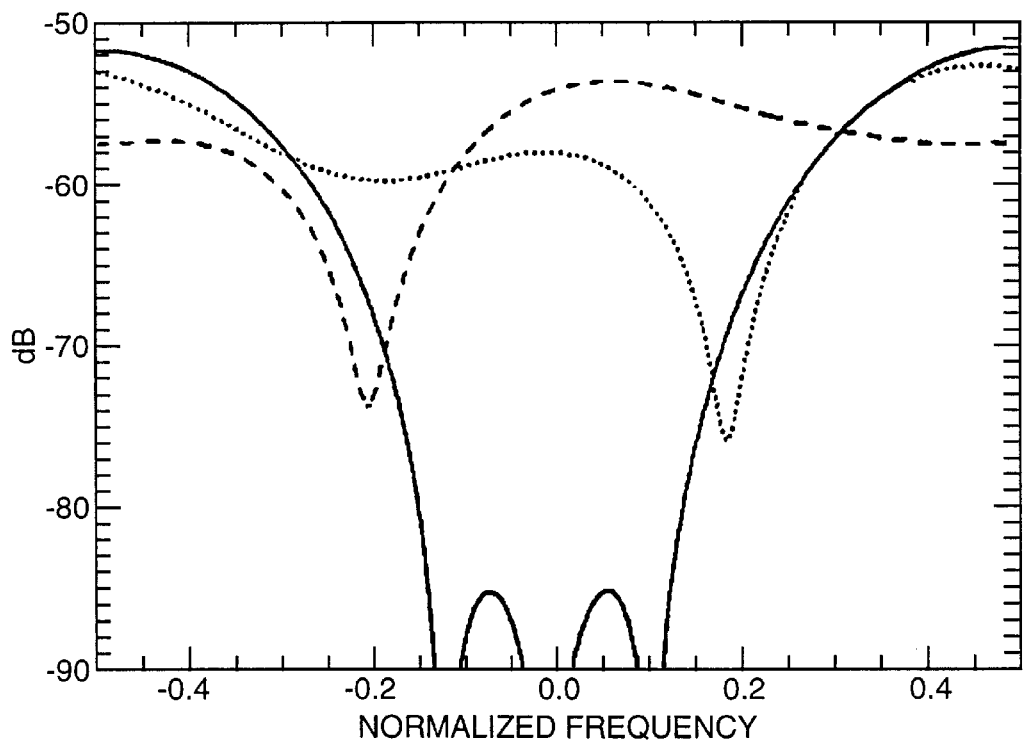

In accordance with a further preferred embodiment of the invention, the B-mode flow image is superimposed on a conventional B-mode image. This allows the diagnostician to observe the flow of blood relative to known anatomical landmarks during medical diagnosis. This B-mode image feed-through is achieved by perturbing one of the "slow-time" filter weightings. For example, the weighting $a_0$ for the first transmit firing (or for any other transmit firing) can be perturbed by an amount α, as shown in FIG. 3. The B-mode feed-through allows the flow image to be superimposed on top of a conventional B-mode image for display.

Alternatively, the flow image may be superimposed in color on top of a conventional B-mode image for display.

The time interval between each of the N transmits per focal position is user controllable to determine the "slow-time" filter cut-off frequency. A longer interval between each of the N transmits to a particular focal position results in a lower cutoff frequency with higher sensitivity to low velocity flow.

While only certain preferred features of the invention have been illustrated and described, many modifications and changes will occur to those skilled in the art. It is, therefore, to be understood that the appended claims are intended to cover all such modifications and changes as fall within the true spirit of the invention.

We claim:

1. A system for imaging ultrasound scatterers, comprising:

an ultrasound transducer array comprising a plurality of transducer elements;

pulsing means coupled to said transducer array for pulsing selected ones of said transducer elements which form a transmit aperture with a first phase-coded transmit pulse as a function of a first transmit phase code during said first transmit firing and with a second phase-coded transmit pulse as a function of a second transmit phase code during said second transmit firing;

transmit beamforming means coupled to said pulsing means for forming first and second beams during said first and second transmit firings respectively, said first and second beams being focused at substantially the same transmit focal position;

receive beamforming means coupled to said transducer array for forming a first beamsummed receive signal from a first set of receive signals from other selected ones of said transducer elements which form a receive aperture subsequent to said first transmit firing and forming a second beamsummed receive signal from a second set of receive signals from said other selected ones of said transducer elements which form said receive aperture subsequent to said second transmit firing;

filtering means for forming a first filtered signal by applying a first "slow-time" filter weighting $a_0$ to said first beamsummed receive signal and for forming a second filtered signal by applying a second "slow-time" filter weighting $a_1$ to said second beamsummed receive signal;

a vector summer coupled to said filtering means for summing at least said first and second filtered signals to form a "slow-time" filtered signal;

means for processing said "slow-time" filtered signal to form an image signal; and means for displaying an image which is a function of said image signal.

2. The system of claim 1 wherein said filtering means comprise:

means for supplying first and second sets of filter coefficients, said first set of filter coefficients being derived by multiplying a predetermined set of coefficients by said first "slow-time" filter weighting $a_0$ and said second set of filter coefficients being derived by multiplying said predetermined set of coefficients by said second "slow-time" filter weighting $a_1$; and a filter having a signal input coupled to an output of said receive beamforming means, a plurality of filter taps coupled to receive said first and second sets of filter coefficients from said means for supplying first and second sets of filter coefficients, and an output for supplying said first filtered signal in dependence on said first beamsummed receive signal and said first set of filter coefficients and for supplying said second filtered signal in dependence on said second beamsummed receive signal and said second set of filter coefficients.

3. The system of claim 1 wherein $a_0 = a_1$.

4. The system of claim 1 wherein said pulsing means are adapted to pulse said selected transducer elements which form said transmit aperture with a third phase-coded transmit pulse as a function of a third transmit phase code during a third transmit firing; said transmit beamforming means being adapted to form a third beam during said third transmit firing, said third beam being focused at said transmit focal position; said receive beamforming means being adapted to form a third beamsummed receive signal from a third set of receive signals from said selected transducer elements which form said receive aperture subsequent to said third transmit firing; said filtering means being adapted to form a third filtered signal by applying a third "slow-time" filter weighting to said third beamsummed receive signal; and said vector summer being adapted to sum at least said first, second and third filtered signals to form said "slow-time" filtered signal.

5. The system of claim 4 wherein said first through third transmit phase codes are [180°, 0°, 180°] and said first through third "slow-time" filter weightings are [0.5, 1, 0.5].

6. The system of claim 4 wherein said pulsing means are adapted to pulse said selected transducer elements which form said transmit aperture with a fourth phase-coded transmit pulse as a function of a fourth transmit phase code during a fourth transmit firing; said transmit beamforming means are adapted to form a fourth beam during said fourth transmit firing, said fourth beam being focused at said transmit focal position; said receive beamforming means are adapted to form a fourth beamsummed receive signal from a fourth set of receive signals from said selected transducer elements which form said receive aperture subsequent to said fourth transmit firing; said filtering means are adapted to form a fourth filtered signal by applying a fourth "slow-time" filter weighting to said fourth beamsummed receive signal; and said vector summer is adapted to sum at least said first through fourth filtered signals to form said "slow-time" filtered signal.

7. The system of claim 6 wherein said first through fourth transmit phase codes are [0°, 180°, 0°, 180°] and said first through fourth "slow-time" filter weightings are [0.4, 1, 1, 0.4].

8. The system of claim 6 wherein said first through fourth transmit phase codes are [0°, 90°, 0°, 180°], said first through fourth "slow-time" filter weightings are [0.4, 1, 1, 0.4], and first through fourth filter phases are [0°, 90°, 0°, 0°], said first through fourth filter phases being respectively adapted to be applied to said filtering means in conjunction with said first through fourth "slow-time" filter weightings.

9. The system of claim 6 wherein said first through fourth transmit phase codes are [0°, 180°, 180°, 0°] and said first through fourth "slow-time" filter weightings are [0.4, 1, −1, −0.4].

10. The system of claim 6 wherein said first through fourth transmit phase codes are [0°, 0°, 180°, 180°] and said first through fourth "slow-time" filter weightings are [1, 1, 1, 1].

11. The system of claim 6 wherein said first through fourth transmit phase codes are [0°, 180°, 180°, 0°] and said first through fourth "slow-time" filter weightings are [1, 1, 1, 1].

12. The system of claim 6 wherein said first through fourth transmit phase codes are [0°, 180°, 0°, 180°] and said first through fourth "slow-time" filter weightings are [1, 1, −1, −1].

13. The system of claim 6 wherein said first through fourth transmit phase codes and said first through fourth "slow-time" filter weightings are selected so that said filtering means can high-pass filter a second harmonic signal and substantially suppress a fundamental signal.

14. The system of claim 6 wherein said first through fourth transmit phase codes and said first through fourth "slow-time" filter weightings are selected so that said filtering means can high-pass filter a fundamental signal and a second harmonic signal.

15. The system of claim 6 wherein said first through fourth transmit phase codes and said first through fourth "slow-time" filter weightings are selected so that said filtering means can all-pass filter a second harmonic signal and substantially suppress a fundamental signal.

16. The system of claim 6 wherein said first through fourth transmit phase codes and said first through fourth "slow-time" filter weightings are selected so that said filtering means can all-pass filter a second harmonic signal and high-pass filter a fundamental signal.

17. A method for imaging ultrasound scatterers, comprising the steps of:
selecting a first transmit phase code and a first "slow-time" filter weighting for a first transmit firing, and a second transmit phase code and a second "slow-time" filter weighting for a second transmit firing;
driving a first set of transducer elements forming a transmit aperture in a transducer array with a first phase-coded transmit pulse as a function of said first transmit phase code during said first transmit firing, said first transmit beam being focused at a transmit focal position;
receiving a first set of echo signals from a second set of transducer elements forming a receive aperture in the transducer array subsequent to said first transmit firing;
forming a first beamsummed receive signal from said first set of echo signals;
forming a first filtered signal by applying a first "slow-time" filter weighting $a_0$ to said first beamsummed receive signal;
driving said first set of transducer elements with a second phase-coded transmit pulse as a function of said second transmit phase code during said second transmit firing, said second transmit beam being focused at said transmit focal position;
receiving a second set of echo signals from said second set of transducer elements subsequent to said second transmit firing;
forming a second beamsummed receive signal from said second set of echo signals;
forming a second filtered signal by applying a second "slow-time" filter weighting $a_1$ to said second beamsummed receive signal;
summing at least said first and second filtered signals to form a "slow-time" filtered signal;
processing said "slow-time" filtered signal to form an image signal; and
displaying an image which is a function of said image signal.

18. The method of claim 17 wherein said first filtered signal is a function of said first beamsummed receive signal and a first set of filter coefficients derived by multiplying a predetermined set of coefficients by said first "slow-time" filter weighting $a_0$, and said second filtered signal is a function of said second beamsummed receive signal and a second set of filter coefficients derived by multiplying said predetermined set of coefficients by said second "slow-time" filter weighting $a_1$.

19. The method of claim 17 wherein $a_0=a_1$.

20. A method for imaging ultrasound scatterers in a flowing fluid medium, comprising the steps of:
selecting a first transmit phase code and a first "slow-time" filter weighting for a first transmit firing, and a second transmit phase code and a second "slow-time" filter weighting for a second transmit firing;
injecting a contrast agent into the flowing fluid medium;
driving a first set of transducer elements forming a transmit aperture in a transducer array with a first phase-coded transmit pulse as a function of said first transmit phase code during said first transmit firing, said first transmit beam being focused at a transmit focal position;
receiving a first set of echo signals from a second set of transducer elements forming a receive aperture in the transducer array subsequent to said first transmit firing;
forming a first beamsummed receive signal from said first set of echo signals;
forming a first filtered signal by applying a first "slow-time" filter weighting $a_0$ to said first beamsummed receive signal;
driving said first set of transducer elements with a second phase-coded transmit pulse as a function of said second transmit phase code during said second transmit firing, said second transmit beam being focused at said transmit focal position;
receiving a second set of echo signals from said second set of transducer elements subsequent to said second transmit firing;
forming a second beamsummed receive signal from said second set of echo signals;
forming a second filtered signal by applying a second "slow-time" filter weighting $a_1$ to said second beamsummed receive signal;
summing at least said first and second filtered signals to form a "slow-time" filtered signal;
processing said "slow-time" filtered signal to form an image signal; and
displaying an image which is a function of said image signal.

21. A system for imaging ultrasound scatterers, comprising:
a transducer array comprising a plurality of ultrasound transducer elements;
means for controlling said transducer array to transmit a first transmit ultrasound beam having a first phase toward said ultrasound scatterers during a first transmit firing and to transmit a second transmit ultrasound beam having a second phase different than said first phase toward said ultrasound scatterers during a second transmit firing;
means for acquiring data from said transducer array representing a first receive ultrasound beam derived from reflections of said first transmit ultrasound beam from said ultrasound scatterers and data from said transducer array representing a second receive ultrasound beam derived from reflections of said second transmit ultrasound beam from said ultrasound scatterers;

means for filtering said first receive ultrasound beam data to form a first filtered signal following said first transmit firing and for filtering said second receive ultrasound beam data to form a second filtered signal following said second transmit firing, said first filtered signal being a function of a first "slow-time" filter weighting and said second filtered signal being a function of a second "slow-time" filter weighting;

means for summing at least said first and second filtered signals to form a "slow-time" filtered signal;

processing means for producing an image signal which is a function of said "slow-time" filtered signal; and means for displaying an image which is a function of said image signal.

22. The system of claim 21 wherein:

said transducer array controlling means is adapted to control said transducer array to transmit a third transmit ultrasound beam having a third phase toward said ultrasound scatterers during a third transmit firing;

said data acquiring means is adapted to acquire data from said transducer array representing a third receive ultrasound beam derived from reflections of said third transmit ultrasound beam from said ultrasound scatterers;

said filtering means is adapted to filter said third receive ultrasound beam data to form a third filtered signal following said third transmit firing, said third filtered signal being a function of a third "slow-time" filter weighting; and said summing means is adapted to sum at least said first, second and third filtered signals to form said "slow-time" filtered signal.

23. The system of claim 22 wherein:

said transducer array controlling means is adapted to control said transducer array to transmit a fourth transmit ultrasound beam having a fourth phase toward said ultrasound scatterers during a fourth transmit firing;

said data acquiring means is adapted to acquire data from said transducer array representing a fourth receive ultrasound beam derived from reflections of said fourth transmit ultrasound beam from said ultrasound scatterers;

said filtering means is adapted to filter said fourth receive ultrasound beam data to form a fourth filtered signal following said fourth transmit firing, said fourth filtered signal being a function of a fourth "slow-time" filter weighting; and said summing means is adapted to sum at least said first through fourth filtered signals to form said "slow-time" filtered signal.

* * * * *